US006537344B2

(12) United States Patent
Mukherjee et al.

(10) Patent No.: US 6,537,344 B2
(45) Date of Patent: Mar. 25, 2003

(54) PROCESS FOR THE PREPARATION OF A NANOSIZED COLLOIDAL METAL PARTICLE

(75) Inventors: Priyabrata Mukherjee, Pune (IN); Deendayal Mandal, Pune (IN); Absar Ahmad, Pune (IN); Murali Sastry, Pune (IN); Rajiv Kumar, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/813,110

(22) Filed: Mar. 20, 2001

(65) Prior Publication Data

US 2002/0174743 A1 Nov. 28, 2002

(51) Int. Cl.$^7$ .................................................. B22F 9/00
(52) U.S. Cl. ........................................... 75/362; 75/744
(58) Field of Search ..................................... 75/362, 744

(56) References Cited

U.S. PATENT DOCUMENTS

| 4,293,333 A | * | 10/1981 | Drobot ........................ 210/601 |
| 4,448,886 A | * | 5/1984 | Gestaut et al. .............. 204/294 |
| 4,898,827 A | * | 2/1990 | Brierley et al. ............. 210/601 |
| 5,698,483 A | * | 12/1997 | Ong et al. ................... 423/111 |

* cited by examiner

Primary Examiner—Roy King
Assistant Examiner—Andrew Wessman
(74) Attorney, Agent, or Firm—Ladas & Parry

(57) ABSTRACT

The invention relates to a biological process for the preparation of nano-sized colloidal metal particles by treating wet fungus or fungus extract with a metal ion solution of the desired metal and separating the biomass to obtain the nano-sized colloidal metal particles.

13 Claims, No Drawings

PROCESS FOR THE PREPARATION OF A NANOSIZED COLLOIDAL METAL PARTICLE

FIELD OF THE INVENTION

The present invention relates to a process for the preparation of a nano sized colloidal metal particle. More particularly, the present invention relates to a process for the preparation of a nano sized colloidal metal particle using naturally occurring bio-materials.

BACKGROUND OF THE INVENTION

Nanoparticles are extremely important materials with utility in different areas ranging from nano-technology, non-linear optics, diode lasers, smart sensors, markers in drugs, gene sequencing to catalysts. In the art, nano materials are obtained by different chemical and physical methods. Chemical methods for the preparation of nano-materials include borohydride and citrate reduction methods for the preparation of colloidal metal such a gold and silver [Handley D. A., *Colloidal Gold: Principles, Methods and Applications,* Hayat M. A.ed., Academic Press, San Diego Calif., 1989, Vol. 1, Chapter 2]. Physical methods for the preparation of nano materials include vapour deposition, lithographic processes and molecular beam epitaxy (MBE). Reduction of metal ions by radiolysis is also frequently used for the preparation of nano-sized metal particles.

However, the prior art methods described above suffer from several drawbacks. The chemical methods are environmentally hazardous and result in quick agglomeration of nano-particles leading to big particles of poor monodispersity. While specific capping agents are used in some of the above methods to restrict the size of the colloidal metal particles and to stabilise the particle size distribution, use of such capping agents makes the system complicated and user—unfriendly. The radiolysis method is quite complicated and gamma ray sources are not readily available.

Accordingly, it is important to develop processes for the preparation of nano-particles which overcome the drawbacks enumerated above.

OBJECTS OF THE INVENTION

The main object of the invention is to provide a process for the preparation of nano sized colloidal metal particles that is environmentally friendly.

It is another object of the invention to provide a process for the preparation of nano-sized colloidal metal particles that is user friendly.

It is a further object of the invention to provide a process for the preparation of nano-sized colloidal metal particles that results in colloidal metal particles with improved stability in aqueous solution.

It is another object of the invention to provide an economic and efficient process for the preparation of nano-sized colloidal metal particles.

These and other objects of the invention are achieved by the process of the invention which uses a biological method for the preparation of nano-sized colloidal metal particles.

SUMMARY OF THE INVENTION

Accordingly the present invention provides a process for the preparation of nano-sized colloidal metal particles, said process comprising treating wet fungus or fungus extract with a metal ion solution at a temperature in the range of 15 to 40° C. for a time period ranging between 2 to 120 hours, separating the biomass to obtain the nano-sized colloidal metal particles.

In one embodiment of the invention, the concentration of the metal ions in the solution ranges from 0.01 to 0.2 g per gram of the wet fungus mycelial mass.

In another embodiment of the invention, the metal ion solution is prepared by dissolving the desired metal salt or acid in water.

In yet another embodiment of the invention, the metal ions comprise metal from Group IB to VIIIB of the periodic table.

In a further embodiment of the invention, the metal ions are selected from the group consisting of Au, Ag, Pd, Pt, Ni, Rh and Ru.

In another embodiment of the invention, the metal salt used for the preparation of the metal ion solution is selected from the group consisting of halide, carbonate and nitrate.

In a further embodiment of the invention, the concentration of the metal ion per gram of the wet fungus or fungus extract is in the range of 10 to 200 mg.

In a further embodiment of the invention, the concentration of the metal ion per gram of the wet fungus or fungus extract is in the range of 10 to 100 mg.

In a further embodiment of the invention, the concentration of the metal ion per gram of the wet fungus or fungus extract is in the range of 25 to 100 mg.

In another embodiment of the invention, the ratio of water to wet fungus or fungus extract ranges between 1:100 (w/w).

In another embodiment of the invention, the fungus used is selected from different species of *Fusarium oxysporum*.

In a further embodiment of the invention, the fungus is used in the form of a whole cell wet solid mass or a fungus extract.

In another embodiment of the invention, the reaction of the fungus and the metal ion source is carried out in water.

In another embodiment of the invention, the temperature for incubation is in the range of 23–33° C., preferably 25–29° C.

DETAILED DESCRIPTION OF THE INVENTION

The process of the invention is described hereinbelow with reference to the following examples, which are illustrative and should not be construed as limiting the scope of the invention.

EXAMPLE 1

10 g of wet fungus *Fusarium oxysporum* which was grown in a culture medium, separated from the medium by centrifugation, washed several times with water through centrifugation, was taken in an autoclaved conical flask and then 100 ml solution of 110 mg of $HAuCl_4$ in water were added and the conical flask was then plugged with cotton and incubated at 27° C. The samples were collected from time to time by filtration of the solution containing the fungus inside the inoculation chamber under laminar flow condition. The samples were collected at different times between 2 and 120 hours and each sample was characterised by UV-Vis spectrscopy followed by fluorescence spectroscopy. The formation of purple coloration and the characteristic plasmon resonance band of gold ca 533 nm are the clear indication of the formation of gold nanoclusters by the reduction of HAuCl$_4$ by the fungus. The samples were also characterised by TEM where the particle size is found to be in the range of 5–71 nm. The samples were further characterised by X-ray diffraction. The reflection at 2θ=38° C. clearly indicates the (111) Bragg reflection of gold nanoclusters. The size of the nanoclusters was also determined from the line broadening of the (111) reflection X-ray and found to be 5–70 nm for the gold nano-particles. The variation of particle size and percent conversion of Au$^{3+}$ into Au$^0$ with the reaction time are shown in Table 1.

TABLE 1

| Time, hours | Particle size nm | Percent reduction of Au$^{3+}$ into Au$^0$ |
|---|---|---|
| 2 | 5 | 5 |
| 5 | 7 | 15 |
| 9 | 10 | 20 |
| 15 | 15 | 25 |
| 20 | 25 | 35 |
| 32 | 35 | 45 |
| 48 | 45 | 50 |
| 60 | 55 | 55 |
| 72 | 60 | 60 |
| 84 | 65 | 65 |
| 96 | 68 | 70 |
| 120 | 70 | 75 |

EXAMPLE 2

10 g of wet fungus *Fusarium oxysporum* which was grown in a culture medium, separated from the medium by centrifugation, washed several times with water through centrifugation, was taken in an autoclaved conical flask and then a solution containing 25 mg of HAuCl$_4$ in 100 ml water were added and the conical flask was then plugged with cotton and incubated at 27° C. The samples were collected from time to time by filtration of the solution containing the fungus inside the inoculation chamber under laminar flow condition. The samples were collected at different times between 2 and 72 hours and each sample was characterised by UV-Vis spectrscopy followed by fluorescence spectroscopy. The formation of purple coloration and the characteristic plasmon resonance band of gold ca 533 nm are a clear indication of the formation of gold nanoclusters by the reduction of HAuCl$_4$ by the fungus. The samples were also characterised by TEM where the particle size is found to be in the range of 5–60 nm. The samples were further characterised by X-ray diffraction. The reflection at 2θ=38° C. clearly indicates (111) Bragg reflection of gold nanoclusters. The size of the nanoclusters was also determined from the line broadening of the (111) reflection X-ray and found to be 5–70 nm for the gold nano-particles.

EXAMPLE 3

10 g of wet fungus *Fusarium oxysporum* which was grown in a culture medium, separated from the medium by centrifugation, washed several times with water through centrifugation, was taken in an autoclaved conical flask and then 250 mg of HAuCl$_4$ in 100 ml water were added and the conical flask was then plugged with cotton and incubated at 27° C. The samples were collected from time to time by filtration of the solution containing the fungus inside the inoculation chamber under laminar flow condition. The samples were collected at different times between 2 and 72 hours and each sample was characterised by UV-Vis spectrscopy followed by fluorescence spectroscopy. The formation of purple coloration and the characteristic plasmon resonance band of gold ca 533 nm are the clear indication of the formation of gold nanoclusters by the reduction of HAuCl$_4$ by the fungus. The samples were also characterised by TEM where the particle size is found to be in the range of 5–90 nm. The samples were further characterised by X-ray diffraction. The reflection at 2θ=38° C. clearly indicates the (111) Bragg reflection of gold nanoclusters.

EXAMPLE 4

10 g of wet fungus *Fusarium oxysporum* which was grown in a culture medium, separated from the medium by centrifugation, washed several times with water through centrifugation, was first inoculated at 27° C. for 12 hours, filtered out and to the 100 g clear total filtrate, taken in a conical flask, 100 mg of HAuCl$_4$ in water were added and kept at 27° C. The samples were collected from time to time by filtration of the solution containing the fungus inside the inoculation chamber under laminar flow condition. The samples were collected between 2 to 72 hours and each sample was characterised by UV-Vis spectrscopy followed by fluorescence spectroscopy. The formation of purple coloration and the characteristic plasmon resonance band of gold ca 533 nm are the clear indication of the formation of gold nanoclusters by the reduction of HAuCl$_4$ by the fungus. The samples were also characterised by TEM where the particle size is found to be in the range of 5–70 nm.

EXAMPLE 5

10 g of wet fungus *Fusarium oxysporum* which was grown in a culture medium, separated from the medium by centrifugation, washed several times with water through centrifugation, was taken in an autoclaved conical flask and then 125 mg of AgNO$_3$ in 100 ml water were added and the conical flask was then plugged with cotton and incubated at 27° C. The samples were collected from time to time by filtration of the solution containing the fungus inside the inoculation chamber under laminar flow condition. The samples were collected between 1 to 86 hours and each sample was characterised by UV-Vis spectrscopy, fluorescence spectroscopy, TEM analysis. The evolution of the plasmon resonance band around 400 nm and the brown colour is a clear indication of the formation of silver nanoclusters. The range of the silver nanoparticle size is found to be 5–80 nm.

EXAMPLE 6

10 g of wet fungus *Fusarium oxysporum* which was grown in a culture medium, separated from the medium by centrifugation, washed several times with water through centrifugation, was taken in an autoclaved conical flask and then 50 mg of AgNO$_3$ in 100 ml water were added and the conical flask was then plugged with cotton and incubated at 37° C. The samples were collected from time to time by filtration of the solution containing the fungus inside the inoculation chamber under laminar flow condition. The samples were collected between 1 to 86 hours and each sample was characterised by UV-Vis spectrscopy, fluorescence spectroscopy, TEM analysis. The evolution of the plasmon resonance band around 400 nm and the brown colour is a clear indication of the formation of silver nanoclusters. The range of the silver nanoparticle size is found to be 5–60 nm.

EXAMPLE 7

10 g of wet fungus *Fusarium oxysporum* which was grown in a culture medium, separated from the medium by centrifugation, washed several times with water through centrifugation, was taken in an autoclaved conical flask and then 75 mg of $AgNO_3$ in 100 ml water were added and the conical flask was then plugged with cotton and incubated at 17° C. The samples were collected from time to time by filtration of the solution containing the fungus inside the inoculation chamber under laminar flow condition. The samples were collected at 1, 2, 6, 19, 25, 30, 40, 46, 52 and 86 hours and each sample was characterised by UV-Vis spectrscopy, fluorescence spectroscopy, TEM analysis. The evolution of the plasmon resonance band around 400 nm and the brown colour is a clear indication of the formation of silver nanoclusters. The range of the silver nanoparticle size is found to be in the range of 5–40 nm.

EXAMPLE 8

10 g of wet fungus Fusarium oxysporum which was grown in a culture medium, separated from the medium by centrifugation, washed several times with water through centrifugation, was taken in an autoclaved conical flask and then 100 mg of $AgNO_3$ in 100 ml water were added and the conical flask was then plugged with cotton and incubated at 27° C. The samples were collected from time to time by filtration of the solution containing the fungus inside the inoculation chamber under laminar flow condition. The samples were collected at 1, 2, 6, 19, 25, 30, 40, 46, 52 and 86 hours and each sample was characterised by UV-Vis spectrscopy, fluorescence spectroscopy, TEM analysis. The evolution of the plasmon resonance band around 400 nm and the brown colour is a clear indication of the formation of silver nanoclusters. The range of the silver nanoparticle size is found to be in the range of 5–80 nm.

EXAMPLE 9

10 g of wet fungus Fusarium oxysporum which was grown in a culture medium, separated from the medium by centrifugation, washed several times with water through centrifugation, was taken in an autoclaved conical flask and then 100 ml solution containing 100 mg of $NiSO_4$ (nickel sulphate) were added and the conical flask was then plugged with cotton and incubated at 22° C. The samples were collected from time to time by filtration of the solution containing the fungus inside the inoculation chamber under laminar flow condition. The samples were collected at 1, 2, 6, 19, 25, 30, 40, 46, 52 and 86 hours and each sample was characterised by UV-Vis spectrscopy, TEM analysis and fluorescence spectroscopy. The evolution of the plasmon resonance band around 415 nm is a clear indication of the formation of Ni-nanoclusters. The nano-particles size is found to be in the range of 5–100 nm.

EXAMPLE 10

10 g of wet fungus Fusarium oxysporum which was grown in a culture medium, separated from the medium by centrifugation, washed several times with water through centrifugation, was taken in an autoclaved conical flask and then 25 mg $NiSO_4$ in 100 ml water were added and the conical flask was then plugged with cotton and incubated at 25° C. The samples were collected from time to time by filtration of the solution containing the fungus inside the inoculation chamber under laminar flow condition. The samples were collected between 1 and 96 hours and each sample was characterised by UV-Vis spectrscopy, TEM analysis and fluorescence spectroscopy. The brown coloration, evolution of the plasmon resonance band around 415 nm and TEM analysis indicated the formation of Ni-nanoclusters in the range of 10–100 nm.

EXAMPLE 11

10 g of wet fungus Fusarium oxysporum which was grown in a culture medium, separated from the medium by centrifugation, washed several times with water through centrifugation, was taken in an autoclaved conical flask and 100 ml aqueous solution containing 125 mg $H_2PtCl_6$ (chloroplatinic acid) in water were added and the conical flask was then plugged with cotton and incubated at 33° C. The samples were collected from time to time by filtration of the solution containing the fungus inside the inoculation chamber under laminar flow condition. The samples were collected between 1 and 96 hours and each sample was characterised by UV-Vis spectroscopy, fluorescence spectroscopy and TEM analysis. The evolution of the plasmon resonance band at 215 nm is a clear indication of formation of Pt nano-particles in the solution. The samples were further characterised by TEM analysis where the particle size was found to be in the range of 10–50 nm.

ADVANTAGES OF THE INVENTION

The main advantage of the present invention is the use of naturally occurring fungi under aqueous medium. Another major advantage of the present invention is that the colloidal nano-sized metal particles formed are quite stable in the aqueous solution. The method of the invention is also environmentally friendly and simple. The reduction process is extracellular with the formation of the nano-particles occurring in the solution and not inside the fungal cell.

We claim:

1. A process for the preparation of nano-sized colloidal metal particles, said process comprising treating fungal mycelia of Fusarium oxysporum or an aqueous extract thereof with an aqueous metal ion solution at a temperature in the range of 15 to 40° C. for a time period ranging between 2 to 120 hours, separating the fungal mycelia or aqueous extract thereof from an aqueous solution containing the colloidal metal particles, to obtain the nano-sized colloidal metal particles of particle size of 5 to 100 nm.

2. The process as claimed in claim 1 wherein the amount of the metal ions in the solution is in the range of 0.01 to 0.2 gram per gram of the fungal mycelia or aqueous extract thereof.

3. The process as claimed in claim 1 wherein the metal ion solution is prepared by dissolving a salt or acid containing the metal in water.

4. The process as claimed in claim 1 wherein the metal ions comprise metals selected from Group IB to VIIIB of the Periodic table.

5. The process as claimed in claim 4 wherein the metal ions are selected from the group consisting of Au, Ag, Pd, Pt, Ni, Rh and Ru.

6. The process as claimed in claim 3 wherein the metal salt used for the preparation of the metal ion solution is selected from the group consisting of halide, carbonate and nitrate.

7. The process as claimed in claim 1 wherein the amount of the metal ion is in the range of 10 to 200 mg per gram of the fungal mycelia or aqueous extract thereof.

8. The process as claimed in claim 7 wherein the amount of the metal ion is in the range of 10 to 100 mg per gram of the fungal mycelia or aqueous extract thereof.

9. The process as claimed in claim 7 wherein the amount of the metal ion is in the range of 25 to 100 mg per gram of the fungal mycelia or aqueous extract thereof.

10. The process as claimed in claim 1 wherein the ratio of water in the aqueous metal ion solution to fungal mycelia or aqueous extract thereof is in the range of 1 to 100 (w/w).

11. The process as claimed in claim 1 wherein the fungal mycelia is taken in the form of a whole mycelia or aqueous extract thereof.

12. The process as claimed in claim 1 wherein the temperature of treatment of the fungal mycelia is in the range of 23–33° C.

13. The process as claimed in claim 12 wherein temperature of treatment of the fungal mycelia is in the range of 25–29° C.

* * * * *